United States Patent
Skak et al.

(10) Patent No.: US 12,403,095 B2
(45) Date of Patent: *Sep. 2, 2025

(54) STABILIZED TACROLIMUS COMPOSITION

(71) Applicant: VELOXIS PHARMACEUTICALS, INC., Cary, NC (US)

(72) Inventors: Nikolaj Skak, Virum (DK); Per Holm, Vanlose (DK)

(73) Assignee: VELOXIS PHARMACEUTICALS, INC., Cary, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/857,442

(22) Filed: Jul. 5, 2022

(65) Prior Publication Data

US 2023/0101012 A1    Mar. 30, 2023

Related U.S. Application Data

(63) Continuation of application No. 16/188,805, filed on Nov. 13, 2018, now Pat. No. 11,419,823, which is a continuation of application No. 15/405,879, filed on Jan. 13, 2017, now Pat. No. 10,166,190, which is a continuation of application No. 13/029,304, filed on Feb. 17, 2011, now Pat. No. 9,549,918, which is a continuation-in-part of application No. 12/499,034, filed on Jul. 7, 2009, now Pat. No. 8,685,998, which is a continuation-in-part of application No. PCT/DK2008/050130, filed on May 30, 2008.

(60) Provisional application No. 61/305,941, filed on Feb. 18, 2010, provisional application No. 61/079,015, filed on Jul. 8, 2008.

(30) Foreign Application Priority Data

Feb. 17, 2010    (DK) .......................... DK2010-00137

(51) Int. Cl.
*A61K 9/20* (2006.01)
*A61K 9/14* (2006.01)
*A61K 31/436* (2006.01)

(52) U.S. Cl.
CPC ............ *A61K 9/2013* (2013.01); *A61K 9/145* (2013.01); *A61K 9/2077* (2013.01); *A61K 31/436* (2013.01)

(58) Field of Classification Search
CPC ................................ A61K 31/436; A61K 9/10
See application file for complete search history.

(56) References Cited

U.S. PATENT DOCUMENTS

| | | |
|---|---|---|
| 4,716,153 A | 12/1987 | Morishita et al. |
| 5,601,844 A | 2/1997 | Kagayama et al. |
| 5,962,022 A | 10/1999 | Bolt et al. |
| 6,168,806 B1 | 1/2001 | Lee et al. |
| 6,204,243 B1 | 3/2001 | Posanski |
| 6,346,537 B1 | 2/2002 | Hata et al. |
| 6,372,760 B1 | 4/2002 | Kato et al. |
| 6,387,918 B1 | 5/2002 | Yamanaka et al. |
| 6,440,458 B1 | 8/2002 | Yamashita et al. |
| 6,503,883 B1 | 1/2003 | Posanski |
| 6,576,259 B2 | 6/2003 | Yamashita et al. |
| 6,761,895 B2 | 7/2004 | Sawada et al. |
| 6,884,433 B2 | 4/2005 | Yamashita et al. |
| 6,884,436 B2 | 4/2005 | Kipp et al. |
| 7,994,214 B2* | 8/2011 | Holm .................. A61K 31/439 424/468 |
| 8,685,998 B2 | 4/2014 | Gordon et al. |
| 2002/0028240 A1 | 3/2002 | Sawada et al. |
| 2003/0180352 A1 | 9/2003 | Patel et al. |
| 2005/0169993 A1 | 8/2005 | Yamashita et al. |
| 2005/0249799 A1 | 11/2005 | Jacob et al. |
| 2006/0045865 A1 | 3/2006 | Jacob et al. |
| 2006/0154953 A1 | 7/2006 | Keri et al. |
| 2006/0159766 A1 | 7/2006 | Jenkins et al. |
| 2006/0177500 A1 | 8/2006 | Shin et al. |
| 2006/0210638 A1 | 9/2006 | Liversidge et al. |
| 2006/0287352 A1 | 12/2006 | Holm et al. |
| 2007/0122482 A1 | 5/2007 | Holm et al. |
| 2008/0153866 A1* | 6/2008 | Woo ..................... A61P 3/10 514/291 |
| 2008/0181947 A1 | 7/2008 | Kojima |
| 2009/0011013 A1 | 1/2009 | Ranklove et al. |
| 2009/0011018 A1 | 1/2009 | Kondo et al. |
| 2010/0008984 A1 | 1/2010 | Holm et al. |
| 2010/0105717 A1 | 4/2010 | Gordon et al. |

FOREIGN PATENT DOCUMENTS

| | | |
|---|---|---|
| EP | 0184162 A2 | 6/1986 |
| EP | 0444659 A2 | 9/1991 |
| EP | 1064942 A1 | 1/2001 |
| EP | 1275373 A1 | 1/2003 |

(Continued)

OTHER PUBLICATIONS

Prajapati et al (International Journal of Pharmaceutics, Aug. 2020, vol. 586, pp. 1-9) (Year: 2020).*
Yadav et al (International Journal of Science and Research Archive, 2023, vol. 09, pp. 474-485) (Year: 2023).*
Overhoff et al (Pharmaceutical Research, Jan. 2008, vol. 25, pp. 167-175) (Year: 2008).*
Skytte et al (J Nat Prod, 2010, vol. 73, pp. 776-779) (Year: 2010).*
Honbo et al., 1987, The oral dosage form of Fk-506, Transplantation Proceedings, vol. 19, No. 5, supplement 6, pp. 17-22.
Nishi et al., 2004, The Expression of Intestinal CYP3A4 in the Piglet Model, Transplantation Proceedings, vol. 36, No. 2, pp. 361-363.
Nishi, et al., 2004, The Colon Displays an Absorptive Capacity of Tacrolimus, Transplantation Proceedings, vol. 36, No. 2, pp. 364-366.

(Continued)

*Primary Examiner* — Mark V Stevens
(74) *Attorney, Agent, or Firm* — Blank Rome LLP

(57) ABSTRACT

The invention relates to a stable pharmaceutical composition comprising comprising a solid dispersion of tacrolimus in a vehicle further comprising e stabilizing agent capable of providing a pH below 7 in the composition, as measured after re-dispersion in water, and preventing or reducing the formation upon storage of major degradation products of tacrolimus, in particular the 8-epitacrolimus.

21 Claims, No Drawings

(56) References Cited

FOREIGN PATENT DOCUMENTS

| | | |
|---|---|---|
| EP | 1275381 A1 | 1/2003 |
| JP | 62277321 A | 12/1987 |
| JP | 02295919 | 12/1990 |
| JP | 200837808 | 2/2008 |
| KR | 20070014872 A | 2/2007 |
| WO | WO-9323022 A1 | 11/1993 |
| WO | WO-9824418 A1 | 6/1998 |
| WO | WO-9949863 A1 | 10/1999 |
| WO | WO-01/37808 | 5/2001 |
| WO | WO-01074359 A1 | 10/2001 |
| WO | WO-0195939 A1 | 12/2001 |
| WO | WO-03004001 A1 | 1/2003 |
| WO | WO-2005004848 A1 | 1/2005 |
| WO | WO-2005020993 A1 * | 3/2005 ............. A61K 31/00 |
| WO | WO-2005087195 A2 | 9/2005 |
| WO | WO-2006062334 A1 | 6/2006 |
| WO | WO-2006083130 A1 * | 8/2006 ........... A61K 31/436 |
| WO | WO-2006136175 A2 | 12/2006 |

OTHER PUBLICATIONS

Sano et al., 2002, Oral FK 506 blood levels are elevated in pig short bowl model: Further investigations with co-administration of an intestinal CYP3A4 inhibitor, Transplantation Proceedings vol. 34, No. 3, pp. 1050-1051.

Tacrolimus (Systemic) Drugs.com, Drug Information Online; http://www.drugs.com/mmx/tacrolimus.hmtl; pp. 1-43; Printed on Oct. 5, 2009.
U.S. Appl. No. 13/167,095, filed Jun. 23, 2011.
U.S. Appl. No. 13/167,160, filed Jun. 23, 2011.
U.S. Appl. No. 13/167,281, filed Jun. 23, 2011.
U.S. Appl. No. 13/167,334, filed Jun. 23, 2011.
U.S. Appl. No. 13/167,420, filed Jun. 23, 2011.
Kjaergaard, et al., Priling—Multiple Core Encapsulation, http://www.niroinic.com/food_Chemical/prilling_encapsulation.asp.
Yang, et al., Int. J. Pharmaceuticals, 1992, vol. 86(2-3), p. 247-257; Abstract only p. 1 of 1.
U.S. Appl. No. 13/167,381, filed Jun. 23, 2011.
U.S. Appl. No. 13/178,280, filed Jul. 7, 2011.
Aqion, pH of Organic Acids, 2012-2017, last modified Apr. 20, 2016 (Year: 2016).
Akashi, et al., (Journal of Pharmaceutical and Biomedical Analysis, 1996, vol. 14, pp. 339-346).
European Medicines Agency (EMA) (Assessment Report for Modigraf—International Nonproprietary Name: Tacrolimus, 2009, p. 1-30).
Formulation in Pharmacy Practice, 2nd edition (Tacrolimus, Aug. 21, 2004 on Wayback Machine).
Chromatography Online, downloaded Oct. 2018; http://www.chromatography-online.org/quant/Chromatographic%20Data/Data%20Processing/Peak%20Area%20Measurements.php (Year 2018).
Aqion, pH of Organic Acids, 2012-2014.
Bolt et al., JP 02295919 A, Derwent English abstract, Dec. 1990.
Skytte et al (J Natl Prod, Feb. 18, 2010, vol. 73, pp. 776-779 (year: 2010).

* cited by examiner

STABILIZED TACROLIMUS COMPOSITION

The present application claims the benefit of Danish Patent Application No. DK 2010-00137 filed Feb. 17, 2010, and U.S. Provisional Application No. 61/305,941, filed Feb. 18, 2010, both of which are hereby incorporated by reference.

The present invention relates to stabilized pharmaceutical compositions comprising tacrolimus. The tacrolimus compositions of the invention comprise a stabilizing agent useful for preventing or reducing the formation of tacrolimus degradation products upon storage. The present invention also relates to a method of preparing a stable pharmaceutical tacrolimus composition.

BACKGROUND OF THE INVENTION

Tacrolimus is a macrolide lactone also known as FK506, fugimycin or tsukubaenolide, which is a pharmaceutically active compound, i.e. a drug substance. A number of tacrolimus formulations are marketed, e.g. under the tradenames Prograf®, Advagraf®, and Protopic®, and used as immunosuppressive agents to prevent allograft rejection, i.e. rejection of transplanted organs. Tacrolimus formulations may also be used topically in a number of conditions.

Tacrolimus is produced by the bacterium *Streptomyces tsukubaensis* and the name is an acronym reportedly derived from "tsukuba macrolide immunosuppressant". Tacrolimus belongs to the class of L-pipecolic acid derived macrolides produced by *Streptomyces* species also comprising for example rapamycin (sirolimus), ascomycin and meridamycin, which may have valuable pharmacological properties.

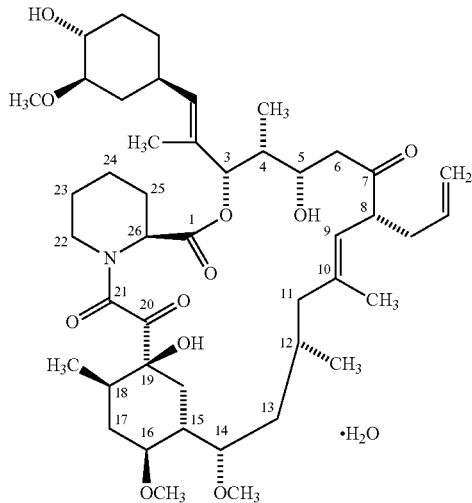

Tacrolimus (USP Tricosine Numbering)

In 2009, the USP issued a draft monograph for tacrolimus monohydrate (Pharmacopeial Forum 35 (2) [March-April 2009], pp. 310-314, USP Pharmacopeial Convention Inc.) using a systematic name for tacrolimus based not on the IUPAC/octacosa-structure convention but on the natural products convention, wherein the base structure is taken to be tricosine (a three-membered macrocycle). This is different from the IUPAC-style nomenclature used in U.S. Pat. No. 4,894,366 for the tacrolimus structure based on a 28-membered ring (octacosa-) numbered clockwise from a carbon in the tetrahydropyran ring.

Tacrolimus exerts its action by binding to the immunophilin FKBP12 to give a complex that inhibits calcineurin, a calcium-dependent phosphatase participating in signal transduction that leads to lymphokine gene transcription.

The presence of degradation products in a pharmaceutical formulation, including a pharmaceutical composition comprising tacrolimus as an active pharmaceutical ingredient, is highly undesirable, since it imposes an increased risk to the patients.

Further, very strict regulatory restrictions exist regarding impurities present in a pharmaceutical formulation, both in a newly prepared pharmaceutical formulation, and in pharmaceutical formulations upon storage, i.e. during their shelf-life. Accordingly, it is necessary to monitor and document the formation of any possible degradation product stemming from the pharmaceutical formulation itself, notably any degradation product arising from the active ingredient, and to either control the amount of degradation product present in the formulation during shelf-life, or to prevent or reduce the formation of degradation product during manufacturing or the shelf-life of the formulation, depending on the nature of each degradation product that may be present or in the pharmaceutical formulation product.

Tacrolimus is a poorly soluble substance, which when administered in crystalline form, is likely to have very low bioavailability due to the relative low amount of liquid available for solubilization in the gastrointestinal tract, especially in the lower part of the intestines including the colon. Accordingly, several attempts have been made to prepare solid solutions, preferably in the form of solid dispersions as also disclosed early in the development of tacrolimus formulations by Hone et al, Transplantation Proceedings, Vol XIX, No 5, Suppl 6 (October), 1987: pp 17-22, which discloses solid dispersions with different formulations. "Establishment of new preparation method for solid dispersion formulation of tacrolimus" by YAMASHITA Kazunari et al, International Journal of Pharmaceutics 2003, vol. 267, no1-2, pp. 79-91 discloses an improved solvent method in order to prevent the use of dichloromethane.

Solvents are generally undesirable in the manufacturing of pharmaceuticals, potential trace amounts need close monitoring, and manufacturing involving solvents is costly. Thus, it is highly desirable for many pharmaceutical companies to be able to prepare solid dispersions without the use of solvents, so that the drug market can be entered with approved products having sufficient absorption capability despite low solubility of the active ingredient. However, the downside of such solid dispersions, especially molecular dispersions, is the motility and the increased exposure of the molecules in the formulation, which increases the risk of chemical degradation compared with conventional crystalline formulations. Identification and prevention of degradation products counts for a considerable part of the cost during development of new pharmaceutical compositions or formulations, and, eventually, otherwise improved formulations may fail to reach the market, if the degradation cannot be controlled in the preferred vehicles of the molecular dispersion of the active ingredient, i.e. the drug substance.

WO2005/020993, WO2005/020994, WO2008/0145143 and WO2010/005980 disclose tacrolimus-containing pharmaceutical compositions with improved bioavailability and a reduced peak-to-trough level as compared to the commercially available tacrolimus products, in particular tacrolimus compositions comprising a solid dispersion of tacrolimus in polyethylene glycol (PEG).

For tacrolimus-containing formulations, in particular formulations containing ingredients which may, as starting materials in the manufacturing process, contain traces of metals or metal compounds, oxidants and other undesirable but unavoidable contaminants, there is a need for preventing the formation of degradation products from tacrolimus or, at least, to maintain an acceptable, low concentration of such degradation products throughout the shelf-life of the formulation, which typically is a formulation in a unit dosage form such as a capsule (soft or hard), a tablet, or granules in a sachet, or as an injection liquid, or as a topical product.

BRIEF SUMMARY OF THE INVENTION

The present invention is directed to stabilized pharmaceutical compositions. According to one embodiment of the invention, the pharmaceutical composition comprises tacrolimus or an analogue of tacrolimus dissolved or dispersed in a vehicle and a stabilizing agent. The stabilizing agent may be a pH-regulating pharmaceutical excipient. Preferably, the stabilizing agent is capable of providing a pH below 7 in the composition, as measured after re-dispersing the composition in water, more preferably a pH in the range of 2.5 to 5 or 2.5 to 4 or 3 to 3.6 or 3 to 3.5. Suitable stabilizing agents include, but are not limited to, inorganic acids, inorganic bases, inorganic salts, organic acids, organic bases, and pharmaceutically acceptable salts thereof. The stabilizing agent can be a chelating agent. For instance, the stabilizing compound can be an organic acid selected from mono-, di-, oligo and polycarboxylic acids, for example succinic acid, citric acid, tartaric acid, acrylic acid, benzoic acid, malic acid, maleic acid, oxalic acid, sorbic acid and mixtures thereof. In one preferred embodiment, the stabilizing agent is oxalic acid, tartaric acid and/or citric acid. One preferred stabilizing agent is tartaric acid.

The composition preferably includes a stabilizing effective amount of stabilizing agent (for instance, an amount effective to prevent or decrease the rate of formation of degradation products). In one embodiment, the amount of stabilizing agent ranges from about 0.05% w/w to about 5% w/w, based upon the total weight of tacrolimus, vehicle and stabilizing agent. The composition can contain at least 0.05% w/w, at least 0.1% w/w, or at least 0.2% w/w and less than 3% w/w, less than 2% w/w, less than 1% w/w, less than 0.8% w/w, or not more than 0.6% w/w of the stabilizing agent.

Suitable vehicles include hydrophilic, amphiphilic or water-miscible polymers. A preferred vehicle is a mixture of a polyethylene glycol and a poloxamer.

The composition can contain less than 0.5% w/w of 8-epitacrolimus, the major degradation product of tacrolimus upon storage. Also, the composition may be substantially free (e.g. contain less than 1, 0.5, 0.2, 0.1 or 0.05% w/w) of an organic solvent or organic solvent residues.

The invention further relates to any oral dosage form including, but not limited to, tablets, capsules and sachets, where the formation of the tacrolimus degradation products disclosed herein (8-epitacrolimus, diene, C4-epimer, Regioisomer A), especially 8-epitacrolimus, is decreased by the presence of a stabilizing agent or excipient such as an organic acid. A preferred organic acid is tartaric acid.

By the present invention, it is possible to prevent or reduce the formation of a possible degradation product in the pharmaceutical formulation, notably any degradation product of tacrolimus, and thereby either control the maximum tolerable amount of degradation product present in the formulation during shelf-life, or to prevent or reduce the formation of degradation product during manufacturing or the shelf-life of the formulation, depending on the nature of the degradation product that may be present or in the pharmaceutical formulation product.

DETAILED DESCRIPTION OF THE INVENTION

The present invention is based on the finding that a very important, i.e. major, degradation product of tacrolimus is the hitherto undisclosed C8-epimer of tacrolimus, also denoted 8-epitacrolimus, having the formula:

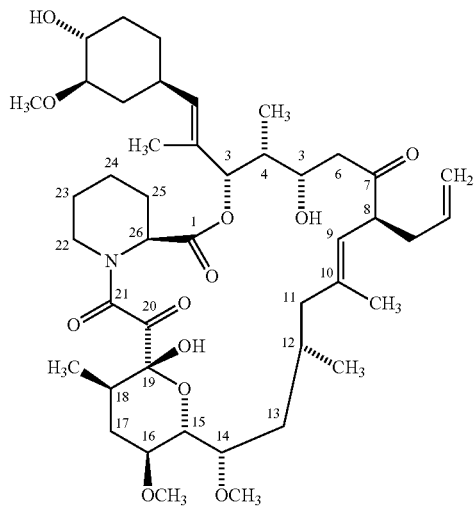

C8-epimer (8-epitacrolimus) (previously denoted C2-epimer)

The structure of 8-epitacrolimus was determined by single-crystal X-ray diffraction using graphite-monochromated Mo Kα radiation (λ=0.71073 Å) on a KappaCCD diffractometer, and data collection using COLLECT and data reduction using EvalCCD (Skytte, D. M. et al.: Synthesis and characterization of an epimer of tacrolimus, an immunosuppresive drug in J. Nat. Prod., 2010 Apr. 23; 73 (4): 776-9, which is hereby incorporated by reference).

This 8S-epimer (isomer) compound was fully characterized by spectroscopic techniques:

8-epitacrolimus (3S, 4R, 5S, 8S, 9E, 12S, 14S, 15R, 16S, 18R, 19R, 26aS)-5,19-dihydroxy-14, 16-dimethoxy-15, 19-epoxy-5,6,8,11,12,13, 14, 15, 16, 17,18, 19,24,25,26, 26a-hexadecahydro-3-[(1E)-2-[(1R,3R,4R)-4-hydroxy-3-methoxycyclohexyl]-1-methylethenyl]-8-(2-propen-1-yl)-4, 10, 12, 18-tetramethyl-3H-pyrido[2,1-c][1,4]oxaazacyclotricosine-1,7,20,21 (4H,23H)-tetrone: Colorless prisms, melting point 179-182° C. [CH$_3$CN—H$_2$O (60:40)]; [α]$^{25}_D$- 1.2 (c 0.725, CHCl$_3$); UV (CH$_3$CN) λ$_{max}$ (ε) 202 nm (9500); CD (CH$_3$CN) λmax ([θ]) 231 (−18 300), 297 (+23 400); IR (KBr) λ$_{max}$ 3580, 3431, 2934, 1753, 1724, 1704, 1633, 1452, 1193, 1170, 1091, 1050 cm$^{-1}$.

It has been found that the formation of 8-epitacrolimus takes place under relatively mild conditions, typically under mild basic conditions. However, it is contemplated that the formation may also take place under mild acidic conditions. Accordingly, this 8S-epimer (an isomer of tacrolimus) may be formed during manipulations of tacrolimus, e.g., during its isolation from fermentation broths, purification, or manufacturing of pharmaceutical formulations, and possibly also in vivo as a metabolite of tacrolimus. Since it is also known that even very minor structural modifications of tacrolimus are known to result in significant alterations of pharmacological profiles (as in the case of ascomycin (Sierra-Paredes et al., CNS Neurosci. Ther. 2008, vol. 14, p. 36-46), an analogue of tacrolimus where the (8R)-propenyl group is replaced by an (8R)-ethyl group), assessment of the biological activity of 8-epitacrolimus is therefore of considerable interest.

Other hitherto undisclosed degradation products of tacrolimus have also been identified by HPLC in a mixture containing tacrolimus:

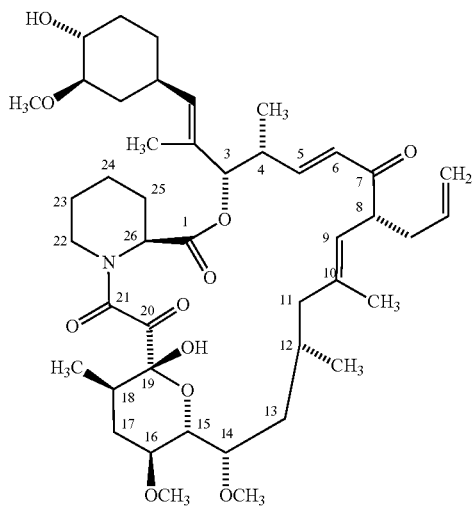

Diene (previously denoted C23-anhydrate)

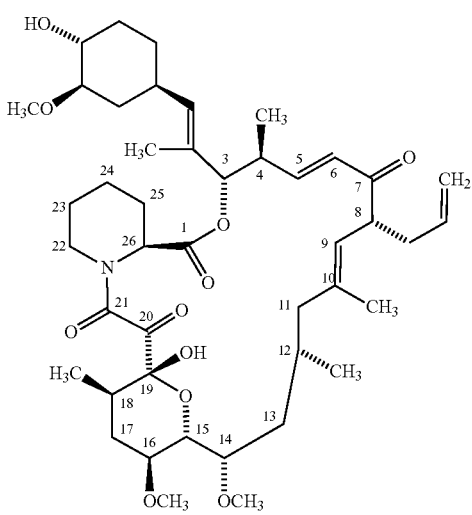

C4-epimer diene (previously denoted C25-epimer-C23-anhydrate)

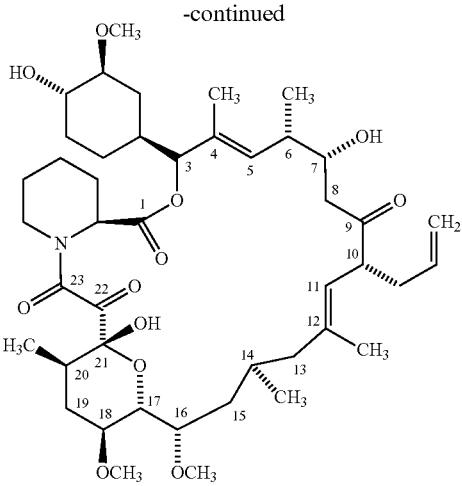

Regio-isomer (previously denoted tautomer 2 back-peak

As used herein, the term "active ingredient" or "active pharmaceutical ingredient" means any component that is intended to furnish pharmacological activity or other direct effect in the diagnosis, cure, mitigation, treatment, or prevention of disease, or to affect the structure or any function of the body of man or other animals. The term includes those components that may undergo chemical change in the manufacture of the drug product and are present in the drug product in a modified form intended to furnish the specified activity or effect.

In the present context, the terms "stabilizing compound", "stabilizing substance" and "stabilizing agent" are used interchangeably.

In the present context, the term "hydrophilic" describes that something 'likes water', i.e. a hydrophilic molecule or portion of a molecule is one that typically is electrically polarized and capable of forming hydrogen bonds with water molecules, enabling it dissolve more readily in water than in oil or other "non-polar" solvents.

In the present context, the term "amphiphilic" describes a molecule (as a surfactant) having a polar water-soluble group attached to a water-insoluble hydrocarbon chain. Thus, one end of the molecule is hydrophilic (polar) and the other is hydrophobic (non-polar).

In the present context, the term "hydrophobic" denotes a compound tending to be electrically neutral and non-polar, and thus preferring other neutral and nonpolar solvents or molecular environments.

As used herein, the term "vehicle" includes, but is not limited to, any solvent or carrier (e.g., a carrier fluid) in a pharmaceutical product that has no pharmacological role. For example, water is the vehicle for xilocaine and propylene glycol is the vehicle for many antibiotics.

As used herein, the term "solid dispersion" denotes a drug substance or an active ingredient dispersed or dissolved in an inert vehicle, carrier, diluent or matrix in solid state. The drug substance or active ingredient may be in the form of particles, often very fine particulate material, or of individual molecules. Accordingly, the term "solid dispersion" includes what is sometimes referred to as a solid solution.

As used herein, the term "analogue" means a chemical compound that is structurally similar to another.

The term "drug" means a compound intended for use in diagnosis, cure, mitigation, treatment, or prevention of disease in man or other animals.

In this context, the term "dosage form" means the form in which the drug is delivered to the patient. This could be parenteral, topical, tablet, oral (liquid or dissolved powder), suppository, inhalation, transdermal, etc.

As used herein, the term "bioavailability" denotes the degree to which a drug or other substance becomes available to the target tissue after administration.

As used herein, the term "bioequivalency" denotes a scientific basis on which generic and brand name drugs are compared with one another. For example, drugs are bioequivalent if they enter circulation at the same rate when given in similar doses under similar conditions. Parameters often used in bioequivalence studies are $t_{max}$, $c_{max}$, $AUC_{0\text{-}infinity}$, $AUC_{0\text{-}t}$. Other relevant parameters may be $W_{50}$, $W_{75}$ and/or MRT. Accordingly, at least one of these parameters may be applied when determining whether bioequivalence is present. Furthermore, in the present context, two compositions are regarded as bioequivalent if the value of the parameter used is within 80-125% of that of Prograf® (e.g., New Drug Application No. 050708 at the U.S. Food and Drug Administration for Prograf) or a similar commercially available tacrolimus-containing product used in the test.

In one embodiment, the pharmaceutical composition of the invention comprises a solid dispersion of tacrolimus in a dispersion medium comprising a vehicle and a stabilizing compound (also referred to as stabilizing agent).

Preferably, pH in the composition is below 7 (as measured by re-dispersion of the composition in water), more preferably, pH is in the range of 2.5-5.0, more preferably from 2.5 to 4.5, even more preferably from 2.5 to 4, even more preferably from 3 to 4, especially from 3.0 to 3.6. The pH may be provided by the stabilizing agent and/or be adjusted by an inorganic or organic acid or a mixture thereof.

Suitable stabilizing compounds and stabilizing agents for use in a composition of the invention include, but are not limited to, inorganic acids, inorganic bases, inorganic salts, organic acids, organic bases and pharmaceutically acceptable salts thereof.

The organic acid is preferably a mono-, di-, oligo or polycarboxylic acid. Non-limiting examples of useful organic acids are acetic acid, succinic acid, citric acid, tartaric acid, acrylic acid, benzoic acid, malic acid, maleic acid, oxalic acid and sorbic acid; and mixtures thereof. Preferred organic acids are selected from the group consisting of oxalic acid, tartaric acid and citric acid.

The pharmaceutically acceptable salt of an organic acid or inorganic acid is preferably an alkali metal salt or an alkaline earth metal salt. Preferred examples of such salts are sodium phosphate, sodium dihydrogen phosphate, disodium hydrogen phosphate, potassium phosphate, potassium dihydrogen phosphate, potassium hydrogen phosphate, calcium phosphate, dicalcium phosphate, sodium sulfate, potassium sulfate, calcium sulfate, sodium carbonate, sodium hydrogen carbonate, potassium carbonate, potassium hydrogen carbonate, calcium carbonate, magnesium carbonate, sodium acetate, potassium acetate, calcium acetate, sodium succinate, potassium succinate, calcium succinate, sodium citrate, potassium citrate, calcium citrate, sodium tartrate, potassium tartrate, calcium tartrate, zinc gluconate, and zinc sulphate.

Suitable inorganic salts include, but are not limited to, sodium chloride, potassium chloride, calcium chloride, and magnesium chloride.

When a composition of the present invention comprises an organic acid as a stabilizing agent, the organic acid is typically present in a concentration of less than 5% w/w, or less than 3% w/w, or less than 2% w/w, or less than 1% w/w, or less than 0.8% w/w, or less than 0.6% w/w, or at least 0.05% w/w, or at least 0.1% w/w, or at least 0.2% w/w, based on the total amount of tacrolimus, vehicle and stabilizing agent.

It has been found that formation of the major degradation product 8-epitacrolimus is decreased in the presence in the composition of a metal chelating agent. Accordingly, the stabilizing agent used in the composition of the present invention is preferably a metal chelating agent, i.e. capable of binding to a metal ion. The metal chelating agent may be an organic acid, preferably citric acid, tartaric acid, oxalic acid or a mixture of any of these acids. For instance, it has been demonstrated that using 0.5% w/w citric acid instead of 0.05% w/w improved the stability of tacrolimus markedly.

Also, as demonstrated in example 3 herein, it has been found that a composition according to the present invention using as a stabilizing agent an organic acid such as tartaric acid in a concentration in the range of about 0.05% w/w to 0.60% w/w will balance the formation the major degradation product 8-epitacrolimus with the formation of three other degradation products, which may also be formed upon storage in the composition. Using tartaric acid in the concentration range of 0.10% w/w to 0.50% w/w is even more preferred, such as the range of from 0.10 to 0.30% w/w, or from 0.10% to 0.20% w/w, such as about 0.15% w/w, based upon the total weight of tacrolimus, vehicle and stabilizing agent.

Thus, in another embodiment of the invention, the stabilizing agent in the tacrolimus composition is tartaric acid. For instance, the composition may include from about 0.01% to about 5% w/w tartaric acid, based upon the total weight of tacrolimus, vehicle and stabilizing agent. The composition may include at least 0.01% w/w tartaric acid, at least 0.05% w/w tartaric acid, at least 0.1% w/w tartaric acid, at least 0.15% w/w tartaric acid, at least 0.2% w/w tartaric acid, at least 0.4% w/w tartaric acid, at least 0.5% w/w tartaric acid, at least 0.6% w/w tartaric acid, at the most 0.75% w/w tartaric acid, at the most 0.8% w/w tartaric acid, at the most 1% w/w tartaric acid, at the most 2% w/w tartaric acid, at the most 3% w/w tartaric acid, or at the most 5% w/w tartaric acid. In a preferred embodiment, the tacrolimus composition contains 0.15% w/w of tartaric acid, based upon the total weight of tacrolimus, vehicle and stabilizing agent.

Also, as shown in the examples herein, tartaric acid and oxalic acid had an improved stabilizing effect as compared to citric acid, when present in the tacrolimus composition of the invention in an amount of 0.5% w/w.

Stabilizing compounds preventing degradation of the active substance as well as specific excipients less prone to interact with tacrolimus or an analogue thereof or degradation products thereof are desired. However, the prevention of degradation products is further complicated by the fact that one excipient added in order to prevent a first degradation, may itself give rise to a second degradation product which may require addition of a further stabilizing excipient. Additionally, prevention of degradation does not always follow a simple linear effect, but windows of optimal effect may exist.

In a still further embodiment of the present invention, the composition comprises 8-epitacrolimus in an amount of less than 0.5% w/w, such as less than 0.2% w/w, based on the total weight of the composition (tacrolimus, vehicle, stabilizing agent).

As demonstrated in the examples, the composition of the present invention is stable and comprises less than 0.5% of 8-epitacrolimus after 12 weeks as well as 10 months of storage at 25° C. at 60% relative humidity.

In a still further embodiment the pharmaceutical composition of the present invention comprises a solid dispersion of tacrolimus in a mixture of a vehicle and a stabilizing agent, wherein the composition contains (a) no more than 0.5% more 8-epitacrolimus after storage at 40° C. at 75% relative humidity for 5 weeks compared to the pharmaceutical composition prior to storage, or (b) no more than 0.2% more 8-epitacrolimus after storage at 25° C. at 60% relative humidity for 5 weeks compared to the pharmaceutical composition prior to storage, or no more than 0.5% more 8-epitacrolimus after storage at 25° C. at 60% relative humidity for 1 year compared to the pharmaceutical composition prior to storage.

The degradation product limit set forth in the International Conference of Harmonization (ICH) guidelines (ICH Topic 3 Q B (R2): Note for Guidance on Impurities in New Drug Products, CPMP/ICH/2738/99, June 2006; www.ema.eu.int) depends on the amount of drug to be administered daily. The daily dosage range for tacrolimus is generally 1 mg to 20 mg. The recommended daily dosage of the commercially available tacrolimus product Prograf® for adult kidney transplant patients (in combination with azothioprine) is 0.2 mg/kg/day (Prograf® tacrolimus capsules; Astellas Pharma US Inc.; product label, 09H011-PRG-WPI, revised August 2009). Assuming the average adult weighs 70 kg, the initial daily dosage of Prograf® would be 14 mg. For a maximum daily dose ranging from 10 to 100 mg, the ICH limit is 0.5% for a single degradation product.

The amount of tacrolimus in the composition of the invention may be any amount useful as a medicament or in preparation of a solid dosage form (e.g., a pharmaceutically effective amount). Typically, the composition comprises from about 0.01% w/w to about 10% w/w of tacrolimus, based upon the total weight of composition, such as from about 0.1% w/w to about 10% w/w of tacrolimus, or from about 0.5% w/w to about 5% of tacrolimus, or from about 1% w/w to about 4% w/w of tacrolimus.

In yet another embodiment of the invention, the vehicle is a hydrophilic, amphiphilic or water-miscible vehicle preferably having a melting point (freezing point or pour point) of at least 20° C., more preferably at least 30° C., more preferably at least 40° C., more preferably at least 50° C., even more preferably at least 52° C., even more preferably at least 55° C., even more preferably at least 59° C., especially at least 61° C., in particular at least 65° C. Preferably, the vehicle is a polymer.

Examples of useful hydrophilic or water-miscible vehicles are substances selected from the group consisting of polyethylene glycols, polyoxyethylene oxides, poloxamers, polyoxyethylene stearates, poly-epsilon caprolactone, polyglycolized glycerides such as Gelucire®, and mixtures thereof. However, also certain amphiphilic vehicles may be useful including those vehicles disclosed herein which may be amphiphilic in addition to being water-miscible.

A preferred vehicle is a polyethylene glycol (PEG), in particular a PEG having an average molecular weight of at least 1500, preferably at least 3000, more preferably at least 4000, especially at least 6000. For example, the PEG may have an average molecular weight ranging from 1500 to 35000, from 3000 to 35000, from 3000 to 20000, from 4000 to 20000, from 3000 to 10000, or from 4000 to 10000. The polyethylene glycol may advantageously be mixed with one or more other hydrophilic or water-miscible vehicles, for example a poloxamer, preferably in a proportion (on a weight/weight basis) of between 1:3 and 10:1, preferably between 1:1 and 5:1, more preferably between and 3:2 4:1, especially between 2:1 and 3:1, in particular about 7:3. A specific example of a useful mixture is a mixture of PEG6000 and poloxamer 188 in the ratio 7:3.

For polyethylene glycols (PEG), the melting point (freezing point or pour point) increases as the average molecular weight increases. For example, PEG 400 is in the range of 4-8° C., PEG 600 is in the range of 20-25° C., PEG1500 is in the range of 44-48° C., PEG2000 is about 52° C., PEG 4000 is about 59° C., PEG 6000 is about 65° C. and PEG 8000 is about 61° C.

Useful poloxamers (also denoted polyoxypropylene-polyoxyethylene block copolymers) are for example poloxamer 188 (having an average molecular weight of about 8400 and a melting point of about 50-54° C.), poloxamer 237, poloxamer 338 or poloxamer 407 or other block copolymers of ethylene oxide and propylene oxide such as the Pluronic® and/or Tetronic® series. Suitable block copolymers of the Pluronic® series include polymers having a molecular weight of about 3,000 or more such as, e.g. from about 4,000 to about 20,000 and/or a viscosity (Brookfield) from about 200 to about 4,000 cps such as, e.g., from about 250 to about 3,000 cps. Suitable examples include Pluronic® F38, P65, P68LF, P75, F77, P84, P85, F87, F88, F98, P103, P104, P105, F108, P123, F123, F127, 10R8, 17R8, 25R5, 25R8 etc. Suitable block copolymers of the Tetronic® series include polymers having a molecular weight of about 8,000 or more such as, e.g., from about 9,000 to about 35,000 and/or a viscosity (Brookfield) of from about 500 to about 45,000 cps such as, e.g., from about 600 to about 40,000. The viscosities given above are determined at 60° C. for substances that are pastes at room temperature and at 77° C. for substances that are solids at room temperature.

Other useful hydrophilic or water-miscible vehicles may be polyvinylpyrrolidones, polyvinyl-polyvinylacetate copolymers (PVP-PVA), polyvinyl alcohol (PVA), polymathacrylic polymers (Eudragit RS; Eudragit RL, Eudragit NE, Eudragit E), cellulose derivatives including hydroxypropyl methylcellulose (HPMC), hydroxypropyl cellulose (HPC), methylcellulose, sodium carboxymethylcellulose, hydroxyethyl cellulose, pectins, cyclo-dextrins, galactomannans, alginates, carragenates, xanthan gums and mixtures thereof.

"Polyglycolized glycerides" denotes a mixture of mono-, di- and triglycerides and polyethylene glycol (PEG) mono- and diesters, preferably of molecular weight between 200 and 600, where appropriate of free glycerol and free PEG, whose HLB value is adjusted by the length of the PEG chain, and whose melting point is adjusted by the length of the chains of the fatty acids, of the PEG and by the degree of saturation of the fatty chains, and hence of the starting oil; examples of such mixtures are Gelucire®. Gelucire® compositions are inert semi-solid waxy materials which are amphiphilic in character and are available with varying physical characteristics. They are surface active in nature and disperse or solubilize in aqueous media forming micelles, microscopic globules or vesicles. They are identified by their melting point/HLB value. The melting point is expressed in degrees Celsius and the HLB (Hydrophile-Lipophile Balance) is a numerical scale extending from 0 to approximately 20. Lower HLB values denote more lipophilic and hydrophobic substances, and higher values denote more hydrophilic and lipophobic substances. The affinity of a compound for water or for oily substances is determined and its HLB value is assigned experimentally. One or a mixture of different grades of Gelucire® excipient may be chosen to achieve the desired characteristics of melting point and/or HLB value. They are mixtures of monoesters, diesters and/or triesters of glycerides of long chain (C12 to C18) fatty acids, and PEG (mono- and/or di) esters of long chain (C12 to C18) fatty acids and can include free PEG. Gelucire® compositions are generally described as fatty acid esters of glycerol and PEG esters or as polyglycolized glycerides. Gelucire® compositions are characterized by a wide range of melting points of from about 33° C. to about 64° C. and most commonly from about 35° C. to about 55° C., and by a variety of HLB values of from about 1 to about 14, most commonly from about 7 to about 14. For example, Gelucire® 50/13 designates a melting point of approximately 50° C. and an HLB value of about 13 to this grade of Gelucire®.

Further examples of substances useful as vehicles are:
  i) polyethoxylated fatty acids such as, e.g. fatty acid mono- or diesters of polyethylene glycol or mixtures thereof such as, e.g. mono- or diesters of polyethylene glycol with lauric acid, oleic acid, stearic acid, myristic acid, ricinoleic acid, and the polyethylene glycol may be selected from PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, PEG 35,000,
  ii) polyethylene glycol glycerol fatty acid esters, i.e. esters like the above-mentioned but in the form of glyceryl esters of the individual fatty acids;
  iii) glycerol, propylene glycol, ethylene glycol, PEG or sorbitol esters with e.g. vegetable oils like e.g. hydrogenated castor oil, almond oil, palm kernel oil, castor oil, apricot kernel oil, olive oil, peanut oil, hydrogenated palm kernel oil and the like,
  iv) polyglycerized fatty acids like e.g. polyglycerol stearate, polyglycerol oleate, polyglycerol ricinoleate, polyglycerol linoleate,
  v) propylene glycol fatty acid esters such as, e.g. propylene glycol monolaurate, propylene glycol ricinoleate and the like,
  vi) mono- and diglycerides like e.g. glyceryl monooleate, glyceryl dioleae, glyceryl mono- and/or dioleate, glyceryl caprylate, glyceryl caprate etc.;
  vii) sterol and sterol derivatives;
  viii) polyethylene glycol sorbitan fatty acid esters (PEG-sorbitan fatty acid esters) such as esters of PEG with the various molecular weights indicated above, and the various Tween® series;
  ix) polyethylene glycol alkyl ethers such as, e.g. PEG oleyl ether and PEG lauryl ether;
  x) sugar esters like e.g. sucrose monopalmitate and sucrose monolaurate;
  xi) polyethylene glycol alkyl phenols like e.g. the Triton® X or N series;
  xii) polyoxyethylene-polyoxypropylene block copolymers such as, e.g., the Pluronic® series, the Synperonic® series, Emkalyx®, Lutrol®, Supronic® etc. The generic term for these polymers is "poloxamers" and relevant examples in the present context are Poloxamer 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407;
  xiii) sorbitan fatty acid esters like the Span® series or Ariacel® series such as, e.g. sorbinan monolaurate, sorbitan monopalmitate, sorbitan monooleate, sorbitan monostearate etc.;
  xiv) lower alcohol fatty acid esters like e.g. oleate, isopropyl myristate, isopropyl palmitate etc.;
  XV) ionic surfactants including cationic, anionic and zwitterionic surfactants such as, e.g. fatty acid salts, bile salts, phospholipids, phosphoric acid esters, carboxylates, sulfates and sulfonates etc.

In a further aspect the present invention relates to a method of preparing a stable pharmaceutical composition comprising a solid dispersion of tacrolimus in a mixture of a vehicle and a stabilizing agent, wherein the pH is from 2.5 to 7 in the composition, as measured after re-dispersion in water, the method comprising the steps of i) dissolving the stabilizing agent in the vehicle and ii) adding or dissolving tacrolimus to vehicle mixture, and iii) optionally adjusting pH of the composition.

WO 2005/020993 discloses tacrolimus formulations which may be useful in combination with the stabilizing agent(s) disclosed herein to yield a stabilized tacrolimus composition. Pharmaceutical compositions and dosage forms which can be optimized to provide the stable composition according to the invention are also exemplified in examples 1-16 of WO 2005/020993, which is hereby incorporated by reference. These exemplified formulations and compositions can be further optimized by adding the stabilizing excipients according to the present invention and as disclosed herein in order to prevent formation of the degradation products as described.

The invention further relates to an oral dosage form of tacrolimus where the formation of the degradation product 8-epitacrolimus is decreased by the presence of a stabilizing agent. The stabilizing agent is preferably an organic acid. A preferred organic acid is tartaric acid. The oral dosage form is preferably an solid dosage form such as tablets, capsules, sachets and other dosage forms conventionally applied for administering drugs to patients in need thereof.

Any combination of the above-described elements in all possible variations thereof is encompassed by the invention unless otherwise indicated herein or otherwise clearly contradicted by context.

List of embodiments:
1. A pharmaceutical composition comprising a solid dispersion of tacrolimus in a mixture of a vehicle and a stabilizing agent capable of providing a pH below 7 in the composition.
2. A composition according to embodiment 1 wherein pH is in the range of 2.5-4.0.
3. A composition according to embodiment 1 wherein pH is in the range of 3.0-3.5.
4. A composition according to embodiment 1 wherein the stabilizing agent is selected from the group consisting of inorganic acids, inorganic bases, inorganic salts, organic acids, organic bases, and pharmaceutically acceptable salts thereof.
5. A composition according to embodiment 1 wherein the stabilizing agent is a chelating compound.
6. A composition according to embodiment 1 wherein the stabilizing agent is an organic acid selected from mono-, di-, oligo and polycarboxylic acids.
7. A composition according to embodiment 3 wherein the organic acid is selected from the group consisting of succinic acid, citric acid, tartaric acid, acrylic acid, benzoic acid, malic acid, maleic acid, and sorbic acid.
8. A composition according to embodiment 7 wherein the organic acid is selected from the group consisting of oxalic acid, tartaric acid, and citric acid.
9. A composition according to embodiment 8 wherein the tartaric acid is present in a concentration of less than 5% w/w, or less than 3% w/w, or less than 2% w/w, or less than 1% w/w, or less than 0.8% w/w, or less than 0.6% w/w, or at least 0.05% w/w, or at least 0.1% w/w, or at least 0.2% w/w, based on the total amount of tacrolimus and vehicle and stabilizing agent.

10. A composition according to embodiment 1, wherein the vehicle comprises a hydrophilic, amphiphilic or water-miscible polymer.

11. A composition according to embodiment 1 wherein the vehicle is a mixture of a polyethylene glycol and a poloxamer.

12. An oral dosage form comprising the pharmaceutical composition according to any of the preceding embodiments.

13. A dosage form according to embodiment 1, which comprises 8-epitacrolimus in an amount of less than 0.5% w/w.

14. A dosage form according to embodiment 1, which comprises an anhydrate degradation product of tacrolimus in an amount of less than 0.5% w/w.

15. A method for reducing the concentration of tacrolimus degradation products in a pharmaceutical composition comprising tacrolimus as the active ingredient, wherein a stabilizing agent is incorporated into the composition.

16. A pharmaceutical composition comprising a dispersion of tacrolimus in a vehicle, wherein the vehicle includes tartaric acid.

17. The pharmaceutical composition of embodiment 16, wherein the composition comprises from about 0.5 to about 5% of tacrolimus, based upon 100% total weight of composition.

18. The pharmaceutical composition of embodiment 16, wherein the composition comprises from about 1 to about 4% tacrolimus, based upon 100% total weight of composition.

19. A pharmaceutical composition comprising a solid dispersion of tacrolimus in a mixture of a vehicle and a stabilizing agent capable of providing a pH below 7 in the composition, wherein the pharmaceutical composition contains the 8-epitacrolimus, and the 8-epitacrolimus is present at a concentration below 0.2% by weight.

20. The pharmaceutical composition of embodiment 19, wherein the solid dispersion is substantially free of organic solvent.

21. A pharmaceutical composition comprising a dispersion of tacrolimus, wherein the composition comprises less than 0.5% of the 8-epitacrolimus after 12 weeks of storage at 25° C. at 60% relative humidity.

22. A pharmaceutical composition comprising a dispersion of tacrolimus, wherein the composition comprises less than 0.5% of the 8-epitacrolimus after 10 months of storage at 25° C. at 60% relative humidity.

23. A pharmaceutical composition comprising a dispersion of tacrolimus, wherein the composition comprises less than 0.5% of the 8-epitacrolimus after 3 weeks of storage at 40° C. at 75% relative humidity.

24. A pharmaceutical composition comprising a dispersion of tacrolimus, wherein the composition comprises less than 0.5% of the 8-epitacrolimus after 19 weeks of storage at 40° C. at 75% relative humidity.

25. A pharmaceutical composition comprising a solid dispersion of tacrolimus in a mixture of a vehicle and a stabilizing agent, wherein the composition contains (a) no more than 0.5% more 8-epitacrolimus after storage at 40° C. at 75% relative humidity for 5 weeks compared to the pharmaceutical composition prior to storage, or (b) no more than 0.2% more 8-epitacrolimus after storage at 25° C. at 60% relative humidity for 5 weeks compared to the pharmaceutical composition prior to storage.

26. A stabilized pharmaceutical composition comprising a solid dispersion of tacrolimus, wherein the composition contains (a) no more than 0.5% of the 8-epitacrolimus, (b) no more than 0.5% of the Diene of tacrolimus, (c) no more than 0.5% of the C4-epimer diene of tacrolimus, and/or (d) no more than 0.5% of Regioisomer A of tacrolimus, after storage at 25° C. at 60% relative humidity for 5 weeks.

27. A stabilized pharmaceutical composition comprising a solid dispersion of tacrolimus, wherein the composition contains (a) no more than 0.5% of the 8-epitacrolimus, (b) no more than 0.5% of the Diene of tacrolimus, (c) no more than 0.5% of the C4-epimer diene of tacrolimus, and/or (d) no more than 0.5% of Regioisomer A of tacrolimus, after storage at 40° C. at 75% relative humidity for 5 weeks.

28. A pharmaceutical composition comprising tacrolimus and from about 0.05 to about 0.6% by weight of tartaric acid.

29. A pharmaceutical composition comprising tacrolimus and tartaric acid at a weight ratio of about 19:0.5 to about 20:6.

Materials and Methods

Materials

Tacrolimus (supplied by Eurotrade)
Lactose monohydrate 200 mesh (from DMV)
Polyethylene glycol 6000, Pluracol® E6000 (from BASF)
Poloxamer 188, Pluronic® F-68 (from BASF)
Magnesium stearate
Croscarmellose sodium, Ac-Di-Sol® (from FMC)
Micro talc
HPMC, i.e. hypromellose sold by ShinEtsu under the tradename Metolose 90SH (type 2910, 2208), Metolose 60SH (type 2910) in various degrees of polymerization (viscosity 3-100,000 cP).
Bead resin, AG 501X8 20-50 Mesh Biotechnology Grade Tablets, capsules or granules might be enteric coated with different types of polymers such as hydroxypropyl-methylcellulose acetate succinate (Aqoat), cellulose acetate phthalate CAP, hydroxypropyl-methylcellulose phtalate HPMCP or methacrylic acid copolymers such as Eudragit L30D, Eudragit 100/S, Eudragit 100/L.

Prograf© Hard Gelatin Capsules, manufactured by Fujisawa Ireland Ltd, are composed of:

| Ingredients | mq |
|---|---|
| Tacrolimus, anhydr. | 1.0 |
| Gelatin | 6.9 |
| Hypromellose | 1.0 |
| Lactose monohydrate | 24.7 |
| Magnesium stearate | 0.3 |
| Shellac | q.s. |
| Soybean lecitine | q.s. |
| Iron oxide red (E172) | q.s. |
| Titanium dioxide (E171) | q.s. |
| Dimeticone (E900) | q.s. |

Methods

In vitro dissolution tests and measurement of pH

The following test methods were applies to the compositions and dosage forms of the present invention.

Test 1—Dissolution:

In vitro dissolution test according to USP Method A, delayed release articles (USP paddle method; rotation speed:

50 rpm; 37° C.; after 2 hours in acidic medium, the medium is changed to phosphate buffer pH 6.8.).

Test 2—Dissolution:

In vitro dissolution test in aqueous dissolution medium adjusted to pH 4.5 (900 ml water with 0.005% HPC (hydroxypropylcellulose) adjusted to pH4.5; 37° C.; USP Paddle method; rotation speed: 50 rpm).

Measurement of pH:

300 mg of the tacrolimus composition of the invention is dispersed in 5 ml of water. A conventional pH-meter is used for measurement of pH in the dispersion.

The following examples serve the purpose of illustrating the invention and are not intended to limiting the scope of the present invention.

Example 1

Tacrolimus Compositions

A. Tacrolimus composition A (tacrolimus tablets) (disclosed in Example 2 of WO2005/020993 and WO 2005/020994)

| Ingredients | % | mg |
|---|---|---|
| Tacrolimus monohydrate | 1.98 | 2.00 |
| Lactose monohydrate | 40.50 | 40.91 |
| Polyethylene glycol 6000 (PEG 6000) | 33.26 | 33.60 |
| Poloxamer 188 | 14.40 | 14.40 |
| Magnesium stearate | 0.50 | 0.51 |
| Talc | 4.50 | 4.55 |
| Croscarmellose sodium | 5.00 | 5.05 |
| Total | 100.00 | 101.01 |

Tacrolimus was dissolved in PEG 6000 at a temperature above 80° C. Poloxamer 188 was added and the solution was heated to a temperature above 80° C. Using feed unit Phast FS1.7, the solution was sprayed onto 200 g of lactose monohydrate in a fluid bed Phast FB100. The resulting granulate was passed through a Comill, sieve no. 1397, 4500 rpm, and blended with croscarmellose sodium for 3 minutes in a Turbula mixer.

Magnesium stearate and talc was sifted through sieve no. 300 and mixed in a Turbula mixer for 3 min. The granulate was mixed with the magnesium stearate: talc (1:9) for 0.5 minutes in a Turbula mixer.

The resulting mixture was compressed into 6 mm tablets of 2 mg active ingredient (100 mg tablet) with compound cup shape.

Mean disintegration time: 7 minutes. Hardness: 65 N

B. Tacrolimus Composition B (Tacrolimus Sustained Release Tablets):

| Ingredients | mg |
|---|---|
| Tacrolimus monohydrate | 2.04 |
| Lactose monohydrate | 41.70 |
| Polyethylene glycol 6000 (PEG 6000) | 34.30 |
| HPMC (type 2208; 15,000 cP) | 63.00 |
| Poloxamer 188 | 14.70 |
| Magnesium stearate | 1.58 |

Tacrolimus was dissolved in PEG 6000 and poloxamer 188 at a temperature above 75° C. Using feed unit Phast FS1.7, the solution was sprayed onto 200 g lactose monohydrate in a fluid bed Phast FB100. The resulting granulate was sieved through 710 mesh, and blended with HPMC for 3 minutes in a Turbula mixer, followed by mixing with the magnesium stearate for 0.5 minutes in a Turbula mixer.

The resulting mixture was compressed into tablets (157 mg tablets) with compound cup shape, each tablet of 2 mg active ingredient. Hardness: 65 N.

Example 2

Stability of Tacrolimus Composition a of Example 1

Tacrolimus composition A of example 1 (2 mg tacrolimus tablets) was stored at 30° C./65% RH (Relative Humidity). At certain time points (start; 1 mth; 2 mths; 3 mths; 6 mths), the composition, in the form of 2 mg tablets, was subjected to a stability test, i.e. analyzed quantitatively by a conventional HPLC assay method for tacrolimus and the major degradation product C8-epimer (8-epitacrolimus). The results shown in the table below demonstrates a pronounced degradation of tacrolimus over time and a significant presence of the C8-epimer degradation product measured as percentage of the total peak area (HPLC).

| | Time point (months) for stability test | | | | |
|---|---|---|---|---|---|
| | 0 mth | 1 mth | 2 mths | 3 mths | 6 mths |
| Tacrolimus (mg) | 2.13 | 1.97 | 2.02 | 1.82 | 1.48 |
| C8-epimer (% of total peak area) | 4.8 | 8.5 | 11.1 | 11.6 | 13.0 |

Example 3

Tacrolimus Compositions Including a Stabilizing Agent (Metal Chelator)

Tacrolimus composition B of example 1 was modified by the addition of a stabilizing agent.

The vehicle of composition B is a mixture of PEG 6000 and poloxamer 188.

Useful stabilizing agents were identified and assessed by testing their ability to dissociate and dissolve in the melted vehicle of tacrolimus composition B of example 1, i.e. 0.5% w/w of each substance (agent), calculated by weight of the total vehicle system, was mixed with PEG/Poloxamer at 80° C., cf. the following table:

| Stabilizing agent (substance) | Physical state in vehicle |
|---|---|
| D-Glucoronic acid | Not dissolved |
| Ethylene di-amine tetra acetic acid (EDTA) | Not dissolved |
| EDTA, $Na_3$ | Not dissolved |
| EDTA, $Na_4$, $2H_2O$ | Not dissolved |
| EDTA, $NH_4$, $H_2O$ | Not dissolved |
| EDTA, Ca, $Na_2$ | Not dissolved |
| Tartaric acid | Dissolved |
| Tartaric acid, K | Not dissolved |
| Tartaric acid, $K_2$, ½$H_2O$ | Not dissolved |
| Tartaric acid, $(NH_4)_2$ | Not dissolved |
| Citric acid, $H_2O$ | Dissolved |
| Citric acid, Na | Not dissolved |
| Citric acid, $Na_3$ | Not dissolved |
| Citric acid, $(NH_4)_2$ | Not dissolved |
| Citric acid, $(NH_4)_3$ | Not dissolved |
| Oxalic acid, $2H_2O$ | Dissolved |
| Oxalic acid, Ca, $xH_2O$ | Not dissolved |
| Triethyleneamine pentaacetic acid, Ca, $Na_3$, $H_2O$ | Not dissolved |

| Stabilizing agent (substance) | Physical state in vehicle |
|---|---|
| 8-hydroxychinoline 0.005%, ½SO₄, ½H₂O | Not dissolved |

Of the tested stabilizing agents, only citric acid, tartaric acid and oxalic acid dissolved in the vehicle mixture. Notably, notwithstanding the ability to dissolve in the used vehicle mixture, these stabilizing agents (chelators) all re-crystallized fully or partly when incorporated in composition B (added to the vehicle during manufacture of composition B according to example 1).

In a first experiment, the use of citric acid as a stabilizing agent was investigated by preparation of two sample compositions (Citric #1 and Citric #2) prepared according to example 1 (composition B) and dissolving 0.05% w/w and 0.5% w/w of citric acid, respectively, in the melted vehicle. The sample compositions were stored at 40° C., 75% RH (relative humidity), and the samples were assayed for the degradation product C8-epimer (8-epitacrolimus) using standard quantitative HPLC after 0, 5 and 16 weeks, cf. the results in the table below.

| Sample Composition | 8-epitacrolimus (percentage of total peak area) | | |
|---|---|---|---|
| | 0 weeks | 5 weeks | 16 weeks |
| Citric #1 (0.05% w/w) | 5.30 | 8.77 | 11.64 |
| Citric #2 (0.5% w/w) | 2.20 | 3.14 | 3.85 |

From the results it is evident that the formation of the degradation product 8-epitacrolimus is considerably higher in the composition containing a low amount (0.05% w/w) of citric acid.

In a second experiment, the use of citric acid, tartaric acid and oxalic acid, respectively, as a stabilizing agent in composition B of example 1 was investigated. The three sample compositions (Citric #3, Oxalic #4, Tartaric #5) were prepared according to example 1 (composition B) and dissolving 0.5% w/w of the stabilizing agent in the melted vehicle. The sample compositions were stored at 25° C./60% RH as well as at 40° C./75% RH, and the samples were assayed for the degradation product C8-epimer (8-epitacrolimus) using quantitative HPLC after 0, 5 and 12 weeks, cf. the results in the table below.

As a comparison, i.e. to investigate whether de-ionization of the vehicle mixture prior to preparation of composition B increased the stability of the composition, a sample composition (Deionized #6) without stabilizing agent but using de-ionized vehicle was prepared according to example 1 (composition B). In the manufacturing of vehicles, traces of e.g. metal ions will inevitably occur in the vehicle due to the use of equipment and excipients containing metal ions.

The vehicle was deionized as follows: 5 g of mixed bead resin was weighed for every 100 g of vehicle. PEG 6000 and poloxamer 188 was melted at 70° C. while stirring. Then the resin was added to the vehicle and the stirring continued for 1 hour. In order to remove the resin, the vehicle was filtered through a 710 mesh and the de-ionized was ready for use. The sample composition Deionized #6 was subjected to the same stability tests as sample compositions #3, #4 and #5.

| Sample Composition No. | | 8-epitacrolimus (percentage of total peak area) | | |
|---|---|---|---|---|
| | | 0 weeks | 5 weeks | 12 weeks |
| Citric #3 | 25° C./60% RH | 0.04 | 0.51 | 0.98 |
| (0.5% w/w) | 40° C./75% RH | 0.04 | 1.67 | 2.56 |
| Oxalic #4 | 25° C./60% RH | 0.10 | 0.22 | n.a. |
| (0.5% w/w) | 40° C./75% RH | 0.10 | 0.45 | 1.01 |
| Tartaric #5 | 25° C./60% RH | 0.02 | 0.10 | 0.23 |
| (0.5% w/w) | 40° C./75% RH | 0.02 | 0.42 | 0.80 |
| Deionized #6 | 25° C./60% RH | 0.85 | 6.76 | 10.36 |
| (comp.) | 40° C./75% RH | 0.85 | 11.43 | 16.35 |

These results show that, in all formulations, the degradation is more pronounced at elevated temperature/relative humidity. Also, the degradation in the comparison sample composition #6 without stabilizing agent is significantly higher than in the sample compositions including a stabilizing agent.

In conclusion, it has been demonstrated that the use of 0.5% w/w of citric acid in tacrolimus composition B of example does improve the stability of tacrolimus markedly in comparison with the use of a lower amount of citric acid (0.05% w/w). A surprisingly better stabilizing effect is, however, obtained by the stabilizing agents (both are metal chelators) tartaric acid and oxalic acid, each in a concentration of 0.5% w/w.

Further experiments carried out in the same manner have surprisingly demonstrated that use of tartaric acid in a concentration in the range of 0.10 to 0.60% w/w effectively decreased the 8-epitacrolimus formation in that the degradation were more pronounced when lower and higher concentrations were used, respectively. However, the quantitative formation of another degradation product with a retention time of 21.5 min were increased with increasing tartaric acid concentration in a linear way and with what seems to be a threshold value corresponding to a percentage of tartaric acid of 0.10% w/w to 0.20% w/w. A further degradation product with a retention time of 4.4 min was additionally observed, especially at low (0.01% w/w) and high concentrations of tartaric acid (0.60% w/w).

Example 4

Addition of Stabilizing Agent in the Manufacturing Process

Two sample compositions #1 and #2 were prepared, the difference being the process step incorporating the stabilizing agent, i.e. either before or after the addition of tacrolimus to the vehicle:

Sample composition #1 (adding tartaric acid and then tacrolimus): 14 g of PEG 6000 and 6 g of poloxamer 188 was melted, stirred, transferred to a petri dish, cooled and crushed (vehicle mixture). 4 g of the vehicle mixture was mixed with 6 mg of tartaric acid, the resulting mixture was heated at 75° C. under stirring for 15 min. Hereafter 160 mg of tacrolimus was added and stirring continued for 2 hours at 75° C. The amount of C8-epimer (8-epitacrolimus) in sample composition #1 was assayed using standard quantitative HPLC at the day of manufacture (day zero) to 0.04% of the total peak area.

Sample composition #2 (adding tacrolimus and then tartaric acid) was prepared in the same way as sample composition #1 apart from the addition of the tartaring acid, which was added after the addition of 160 mg of tacrolimus (the addition steps were reversed). The amount of C8-epimer (8-epitacrolimus) in sample composition #1 was assayed using standard quantitative HPLC at the day of manufacture (day zero) to 1.33% of the total peak area.

In conclusion, it is demonstrated that it is important to stabilize the tacrolimus composition with tartaric acid (being a chelator as well as an acid) also in the manufacturing process steps.

Example 5

Stabilizing Agents for Use in Tacrolimus Compositions

The purpose of this experiment was to investigate the use of organic and inorganic acids as stabilizing agents in compositions of tacrolimus dispersed in a PEG 6000/poloxamer vehicle.

Four sample compositions (#1, #2, #3 and #4) were prepared by melting 14 g of PEG 6000 and 6 g of poloxamer 188 together, stirring, transferring the mixture to a petri dish, cooling and crushing. 4 g of the vehicle mixture was mixed with an amount of stabilizing agent according to the table below, the mixture was heated and stirred at 75° C. for 15 min. Then 160 mg of tacrolimus was added under stirring, which continued for 2 hours at 75° C. pH of the sample composition was measured. The sample compositions were stored at 40° C./75% RH, and the samples were assayed for the degradation product C8-epimer (8-epitacrolimus) using standard quantitative HPLC after 0 and 7 days, cf. the results in the table below.

| Sample Composition No. | Stabilizing agent | pH | C8-epimer (% of total peak) | |
|---|---|---|---|---|
| | | | 0 days | 7 days |
| #1 | None | 7.0 | 2.57 | 3.20 |
| #2 | Tartaric acid, 6 mg | 3.5 | 0.04 | 0.06 |
| #3 | Acetic acid, 150 μL | 3.2 | 1.02 | 1.70 |
| #4 | 1% H$_2$SO$_4$/2-propanol, 300 μL | 3.0 | 3.18 | 3.53 |

The result clearly demonstrates the superiority of tartaric acid at pH 3.5 as stabilizing agent compared to the tested inorganic acids. In contrast to the inorganic acids, tartaric acid has a chelating effect. It is contemplated that a chelator stabilizing agent is preferred in order to prevent or reduce formation of C8-epimer tacrolimus degradation product. It is evident from the data, that there is no stabilizing effect in maintaining a low pH as such; a stabilizing agent, preferably with chelating effect, is necessary.

Example 6

Stabilizing Agents for Use in Tacrolimus Compositions-Using the Same Molar Concentration Use of organic acids with chelating effect as stabilizing agents in the composition of the invention was investigated using the acids in the same molar concentration:

| | pKa: | MW g/mol | |
|---|---|---|---|
| Tartaric Acid | 2.98 | 150.09 | |
| Citric Acid | 3.13 | 210.14 | monohydrate |
| Oxalic Acid | 1.27/4.28 | 126.07 | Dehydrate |

Four sample compositions (#1 Comparison, #2 Tartaric, #3 Citric and #4 Oxalic) were prepared in the same manner as described in Example 5. The sample compositions were stored at 40° C./75% RH, and the samples were assayed for the degradation product C8-epimer (8-epitacrolimus) using standard quantitative HPLC after 0, 10 and 30 days, cf. the results in the table below.

| Sample Composition No. | Stabilizing agent | pH | C8-epimer (% of total peak) | | |
|---|---|---|---|---|---|
| | | | 0 days | 10 days | 30 days |
| #1 Comparison | None | 7.0 | 2.06 | 11.94 | 23.74 |
| #2 Tartaric | Tartaric acid, 6 mg | 3.5 | 0.05 | 0.62 | 1.55 |
| #3 Citric | Citric acid, 8.4 mg | 3.2 | 0.05 | 0.58 | 1.23 |
| #4 Oxalic | Oxalic acid, 5.04 mg | 3.4 | 0.04 | 0.45 | 0.80 |

This experiment shows that the stabilizing effect of citric acid (pH 3.2) and oxalic acid (pH 3.4) were superior to tartaric acid (pH 3.5). However, oxalic acid is conventionally less useful in pharmaceutical compositions for regulatory reasons.

Example 7

Tartaric Acid as Stabilizing Agent in Tacrolimus Compositions-pH Effect

The impact of pH on the stabilizing and chelating effect of tartaric acid in a tacrolimus composition of the invention is investigated by preparation of seven sample compositions comprising the same amount of tartaric acid (chelating effect) but adjusted to different pH with formic acid or trometamol.

Seven sample compositions (#1 pH 3.6, #2 pH 2.2, #3 pH 4.9, #4 pH 5.8, #5 ph 7.1, #6 pH 7.6 and #7 pH 8.0) were prepared in the same manner as described in Example 5. Each sample composition apart from #2 was added 150 μL of a solution containing 300 mg mg tartaric acid in 10 ml 2-propanol and a volume of a solution of 120.49 mg trometamol in 10 ml methanol as listed in the table below. Sample #2 was added 6.012 mg tartaric acid and 400 μL of formic acid. The sample compositions were stored at 40° C./75% RH, and the samples were assayed for the degradation product C8-epimer (8-epitacrolimus) using standard quantitative HPLC after 0 and 14 days, cf. the results in the table below.

| Sample Composition No. | Stabilizing agent | pH adjustment Trometamol solution added (μL) | C8-epimer (% of total peak) | |
|---|---|---|---|---|
| | | | 0 days | 14 days |
| #1 pH 3.6 | Tartaric acid | None | 0.05 | 0.38 |
| #3 pH 4.9 | Tartaric acid | 500 | 0.25 | 2.77 |
| #4 pH 5.8 | Tartaric acid | 580 | 0.44 | 3.75 |
| #5 pH 7.1 | Tartaric acid | 670 | 0.70 | 5.16 |
| #6 pH 7.6 | Tartaric acid | 750 | 0.89 | 5.99 |
| #7 pH 8.0 | Tartaric acid | 830 | 1.18 | 6.77 |

Sample Compositions #1 and #2 were samples were assayed for tacrolimus using standard quantitative HPLC after 0, 11 and 30 days, cf. the results in the table below.

| Sample Composition No. | Stabilizing agent | pH adjustment Formic acid added (µL) | C8-epimer (% of total peak) | | |
|---|---|---|---|---|---|
| | | | 0 days | 11 days | 30 days |
| #1 pH 3.6 | Tartaric acid | None | 97.83 | 93.70 | 92.03 |
| #2 pH 2.2 | Tartaric acid | 400 | 83.32 | 22.59 | 10.25 |

The results demonstrate that pH matters: At pH 2.2 in the tacrolimus composition, there is immediate degradation of tacrolimus, and after 30 days almost all tacrolimus has degraded. At pH 4.9 up to 8.0 it is demonstrated that even a small pH increase has a significant effect on the stability of tacrolimus.

Example 8

Tartaric Acid as Stabilizing Agent in Tacrolimus Compositions-Concentration Optimum Five sample compositions was prepared as described in Example 3 using tacrolimus composition B of Example 1 (2 mg tacrolimus tablet composition) and with the addition of tartaric acid as stabilizing agent in the amount listed in the table below (% w/w calculated by weight of the total amount of vehicle). The sample compositions were stored in HDPE bottles with silica gel desiccant at 25° C./60% RH for up to 10 months, and the samples were assayed for the degradation product C8-epimer (8-epitacrolimus) using standard quantitative HPLC after the time period listed in the table below.

| Conc. of tartaric acid | C8-epimer (% of total peak) measured after storage for (time in months) | | | | | | | | | | |
|---|---|---|---|---|---|---|---|---|---|---|---|
| | 0 | 1 | 1.5 | 2 | 3 | 5 | 6 | 7 | 8 | 9 | 10 |
| 0.05% w/w | — | 0.05 | | | 0.23 | 0.35 | | 0.53 | | | |
| 0.10% w/w | — | — | | | 0.07 | 0.07 | | 0.14 | | | |
| 0.15% w/w | 0.05 | 0.08 | 0.04 | | 0.06 | | | | 0.19 | 0.15 | 0.19 |
| 0.20% w/w | — | — | | 0.07 | | 0.11 | | | | | |
| 0.50% w/w | 0.04 | | | 0.14 | 0.22 | | 0.30 | | | 0.23 | 1.43 |

The results demonstrate the stabilizing effect of tartaric acid in the concentration range from 0.05% w/w to 0.50% w/w, which provides long term stability. The data suggests that, in particular, the concentration range from 0.10 to 0.20% w/w of tartaric acid has the highest stabilizing effect on a tacrolimus composition.

Example 9

Tartaric Acid as Stabilizing Agent for Tacrolimus Compositions Using Different Vehicles In this experiment, the use of stabilizing agent (0.5% w/w tartaric acid, calculated by weight of the total vehicle composition) in a composition of 5% w/w of tacrolimus in a vehicle as listed in the table below was investigated.

11 different vehicle systems were used, and for each vehicle system was prepared a sample composition of 5% w//w of tacrolimus dispersed or dissolved in the vehicle system (reference composition) and a sample composition of 5% w//w of tacrolimus dispersed or dissolved in the vehicle system including 0.5% w/w tartaric acid as stabilizing agent (invention composition). Each sample composition were stored at 40° C./75% RH, and the samples were assayed for the degradation product C8-epimer (8-epitacrolimus) using standard quantitative HPLC after 7 days in terms of percentage of total peak. For each vehicle system, the result in the table below is given as the amount of C8-epimer in the reference composition relative to the amount of C8-epimer in the invention composition.

| Vehicle (tradename) | Vehicle name(s) | Relative amount of C8-epimer |
|---|---|---|
| Acconon MC-8 | Caprylocaproyl Macrogolglycerides PEG-8 Caprylic/ Capric Glycerides | 2.94 |
| Acconon S-35 | Ethoxylated soybean oil glycerol esters PEG-35 Soy Glycerides | 9.50 |
| Brij 700 P | Polyoxyethylene 100 stearyl ether PEG-100 stearyl ether | 510.04 |
| Captex 200 | Propylene Glycol Dicaprylate/Dicaprate | 4.53 |
| Cremophor A 25 | Macrogol cetastearyl ether | 320.83 |
| Cremophor ELP | Polyoxyl 35 castor oil, Macrogol glycerol ricinoleate | 12.21 |
| Grindsted PGMS SPV | Propylene Glycol Ester | 5.70 |
| Labrafil M1944 CS | Oleoyl Macrogol-glucerides, Oleoyl Polyoxylglycerides | 7.80 |
| LipoPEG 6000 DS | PEG-150 Distearate | 35.72 |
| MethoxyPEG 5000 | Methoxypolyethylene Glycol 5000 | 54.90 |
| PEG-dimethylether | PEG-dimethylether | 2.09 |

The results demonstrate the ability of tartaric acid to increase the stability a composition of tacrolimus dispersed or dissolved in a wide variety of vehicles and vehicle polymers.

All publications, patents, and patent applications cited herein are hereby incorporated by reference.

The invention claimed is:
1. A pharmaceutical composition comprising a solid dispersion of tacrolimus in a mixture of a vehicle and a stabilizing agent that is a metal chelating agent and provides a pH below 7 in the composition, wherein
  (i) the composition comprises from about 0.5 to about 5% of tacrolimus, based upon 100% total weight of composition,
  (ii) the composition contains no more than 0.5% more 8-epitacrolimus after storage at 40° C. at 75% relative humidity for 5 weeks compared to the pharmaceutical composition prior to storage, based upon 100% total weight of tacrolimus, and
  (iii) the tacrolimus is the sole active ingredient in the composition, and

(iv) the vehicle does not include a cyclo-dextrin.

2. The composition of claim 1, wherein the pH in the composition is in the range of 2.5 to 4.0.

3. The composition of claim 1, wherein the pH in the composition is in the range of 3.0 to 3.6.

4. The composition of claim 1, wherein the metal chelating agent is an organic acid selected from mono-, di-, oligo- or polycarboxylic acids.

5. The composition of claim 4, wherein the organic acid is selected from the group consisting of succinic acid, citric acid, tartaric acid, acrylic acid, benzoic acid, malic acid, maleic acid, and sorbic acid.

6. The composition of claim 1, wherein the stabilizing agent comprises citric acid.

7. The composition of claim 1, wherein the stabilizing agent comprises tartaric acid.

8. The composition of claim 1, wherein the vehicle is a mixture of polyethylene glycol and poloxamer.

9. The composition of claim 1, wherein the composition comprises about 1% tacrolimus, based upon 100% total weight of composition.

10. The composition of claim 1, wherein a sufficient amount of the stabilizing agent is present in the composition such that the composition comprises less than 0.5% by weight of 8-epitacrolimus after 12 weeks of storage at 25° C. and 60% relative humidity, based upon 100% total weight of tacrolimus.

11. A pharmaceutical composition comprising a solid dispersion of tacrolimus in a mixture of a vehicle and a stabilizing agent that is a metal chelating agent and provides a pH below 7 in the composition, wherein (i) the composition comprises from about 0.5 to about 5% of tacrolimus, based upon 100% total weight of composition, (ii) the composition contains no more than 0.2% more 8-epitacrolimus after storage at 25° C. at 60% relative humidity for 5 weeks compared to the pharmaceutical composition prior to storage, based upon 100% total weight of tacrolimus, (iii) the tacrolimus is the sole active ingredient in the composition, and (iv) the vehicle does not include a cyclo-dextrin.

12. The composition of claim 11, wherein the pH in the composition is in the range of 2.5 to 4.0.

13. The composition of claim 11, wherein the pH in the composition is in the range of 3.0 to 3.6.

14. The composition of claim 11, wherein the metal chelating agent is an organic acid selected from mono-, di-, oligo- or polycarboxylic acids.

15. The composition of claim 14, wherein the organic acid is selected from the group consisting of succinic acid, citric acid, tartaric acid, acrylic acid, benzoic acid, malic acid, maleic acid, and sorbic acid.

16. The composition of claim 11, wherein the stabilizing agent comprises citric acid.

17. The composition of claim 11, wherein the stabilizing agent comprises tartaric acid.

18. The composition of claim 11, wherein the vehicle is a mixture of polyethylene glycol and poloxamer.

19. The composition of claim 11, wherein the composition comprises about 1% tacrolimus, based upon 100% total weight of composition.

20. The composition of claim 11, wherein a sufficient amount of the stabilizing agent is present in the composition such that the composition comprises less than 0.5% by weight of 8-epitacrolimus after 12 weeks of storage at 25° C. and 60% relative humidity, based upon 100% total weight of tacrolimus.

21. The composition of claim 1, wherein the composition is in the form of a tablet.

\* \* \* \* \*